United States Patent [19]
Geerlings et al.

[11] Patent Number: 6,130,184
[45] Date of Patent: Oct. 10, 2000

[54] COBALT BASED FISCHER-TROPSCH CATALYST

[75] Inventors: Jacobus Johannes Cornelis Geerlings; Hans Michiel Huisman; Carolus Matthias Anna Maria Mesters, all of CM Amsterdam, Netherlands

[73] Assignee: Shell Oil Company, Houston, Tex.

[21] Appl. No.: 09/223,548

[22] Filed: Dec. 30, 1998

[30] Foreign Application Priority Data

Dec. 30, 1997 [EP] European Pat. Off. .............. 97310669

[51] Int. Cl.[7] ............................. B01J 23/00; B01J 23/40; B01J 23/42
[52] U.S. Cl. ..................... 502/350; 502/308; 502/309; 502/312; 502/313; 502/324; 502/325; 502/326; 502/349
[58] Field of Search ..................................... 502/325, 326, 502/349, 350, 324, 308, 309, 312, 313

[56] References Cited

U.S. PATENT DOCUMENTS

| | | | |
|---|---|---|---|
| 4,663,305 | 5/1987 | Mauldin et al. | 502/304 |
| 4,962,078 | 10/1990 | Behrmann et al. | 502/325 |
| 4,992,406 | 2/1991 | Mauldin et al. | 502/304 |
| 5,140,050 | 8/1992 | Mauldin et al. | 518/715 |
| 5,780,381 | 7/1998 | Wilson et al. | 502/308 |

FOREIGN PATENT DOCUMENTS

| | | | |
|---|---|---|---|
| 0 455 307 A1 | 11/1991 | European Pat. Off. | B01J 23/00 |
| 0 510 771 A1 | 10/1992 | European Pat. Off. | B01J 37/00 |
| 0 510 772 A1 | 10/1992 | European Pat. Off. | B01J 21/06 |
| WO 97/00231 | 1/1997 | WIPO | C07C 1/00 |
| WO 97/17137 | 5/1997 | WIPO | B01J 37/18 |
| WO 98/11037 | 3/1998 | WIPO | C07C 1/04 |
| WO 98/25870 | 6/1998 | WIPO | C07C 1/04 |

*Primary Examiner*—Mark L. Bell
*Assistant Examiner*—Patricia L. Hailey

[57] ABSTRACT

A process for the preparation of a cobalt-containing catalyst or catalyst precursor, comprising (a) mixing (1) titania or a titania precursor, (2) a liquid, and (3) a cobalt compound, which is at least partially insoluble in the amount of liquid used, to form a mixture, (b) shaping and drying of the mixture thus-obtained, and (c) calcination of the composition thus-obtained. A catalyst or catalyst precursor obtainable by the process as defined, and a process for the preparation of hydrocarbons comprising contacting a mixture of carbon monoxide and hydrogen with the catalyst as defined.

15 Claims, No Drawings

COBALT BASED FISCHER-TROPSCH CATALYST

The present invention relates to a new process for the preparation of a catalyst or catalyst precursor, the catalyst or catalyst precursor thus obtained and a process for the preparation of hydrocarbons from synthesis gas using the new catalyst or catalyst precursor.

The preparation of hydrocarbons from a gaseous mixture comprising carbon monoxide and hydrogen (synthesis gas) by contacting the mixture with a catalyst at elevated temperature and pressure is known in the literature as the Fischer-Tropsch synthesis.

Catalysts used in the Fischer-Tropsch synthesis often comprise one or more metals from Group VIII of the Periodic Table of Elements, especially from the iron group, optionally in combination with one or more metal oxides and/or metals as promoters. Recently, particular interest has been given to catalysts comprising cobalt as the catalytically active component, in combination with one or more promoters selected from zirconium, titanium, chromium, vanadium and manganese, especially manganese, and supported on a titania carrier. Such catalyst are known in the art and have been described, for example in the specifications of International patent application publication No. WO 97/00231 and European Patent Applications No. 96203538.2 and 96202524.3.

Typically, the catalysts in the prior art have been prepared by impregnation of a porous carrier with one or more soluble cobalt salts and a quantity of a solvent, followed by drying, calcination and optionally activation. In the case of pore impregnation of a porous carrier, it will usually be possible to start with a mechanical strong extrudate. However, the maximum cobalt loading that can be obtained by a single impregnation step is restricted by the pore volume of the carrier and the solubility of the cobalt salt. In practice, several impregnation steps are needed to obtain the desired quantity of cobalt. The need for such a number of steps is undesirable for the preparation of catalysts on a commercial scale.

It has been described in the prior art that suitable Fischer-Tropsch catalyst also may be prepared by mulling or kneading alumina (EP 0 455 307), silica (EP 0 510 771) or zirconia (EP 0 510 772) with a soluble or insoluble cobalt source. In that way a paste may be obtained which is extruded, dried and calcined in order to get a catalyst or catalyst precursor which may be used in the Fischer-Tropsch reaction. Especially in the case of using an insoluble cobalt source, a sufficiently high loading of cobalt may be obtained with a relatively simple process, suitable for use on a commercial scale. However, in order to obtain mechanically strong catalysts, the extrudates have to be calcined at relatively high temperatures. The drawback of high calcination temperatures is that the catalyst performance is adversely affected.

Thus, there is a need in the art for mechanically strong Fischer-Tropsch catalysts with a high loading of cobalt, obtained by a simple preparation process, showing a high performance.

Surprisingly, it has now been found that mechanically strong catalysts with a high loading of cobalt and an excellent performance can be prepared by a relatively simple process. In particular, it has been found that the mixing of a partially insoluble cobalt compound, a liquid, and titania prior to shaping, drying and calcining results in a mechanically strong catalyst having a very good activity and $C_5+$ selectivity when used in the process for the preparation of hydrocarbons.

Thus, the present invention relates to a process for the preparation of a cobalt-containing catalyst or catalyst precursor, comprising: (a) mixing (1) titania or a titania precursor, (2) a liquid, and (3) a cobalt compound, which is at least partially insoluble in the amount of liquid used, to form a mixture; (b) shaping and drying of the mixture thus obtained; and (c) calcination of the composition thus obtained.

The process of the present invention advantageously provides a simple process for the preparation of a cobalt-containing catalyst or catalyst precursor, resulting in a mechanically strong catalyst, having a high activity and $C_5+$ selectivity when used in Fischer-Tropsch synthesis.

The titania for inclusion in the mixture may further comprise up to 20% by weight of another refractory oxide, typically silica, alumina or zirconia, or a clay as a binder material, preferably up to 10% by weight based on the total weight of refractory oxide and binder material. Preferably, the titania has been prepared in the absence of sulphur-containing compounds. An example of such preparation method involves flame hydrolysis of titanium tetrachloride. Titania is available commercially and is well-known as material for use in the preparation of catalysts or catalyst precursors. The titania suitably has a surface area of from 0.5 to 200 $m^2/g$, more preferably of from 20 to 150 $m^2/g$.

As an alternative or in addition to titania, the mixture may comprise a titania precursor. Titania may be prepared by heating titania hydroxide. As the heating progresses, titania hydroxide is converted via a number of intermediate forms and the successive loss of a number of water molecules into titania. For the purpose of this specification, the term "titania precursor" is to be taken as a reference to titania hydroxide or any of the aforementioned intermediate forms.

The liquid may be any of suitable liquids known in the art, for example water; ammonia; alcohols, such as methanol, ethanol and propanol; ketones, such as acetone; aldehydes, such as propanal and aromatic solvents, such as toluene. A most convenient and preferred liquid is water.

Any cobalt compound of which at least 50% by weight is insoluble in the amount of the liquid used, can be suitably used in the process of the present invention. Preferably, at least 70% by weight of the cobalt compound is insoluble in the amount of liquid used, more preferably at least 80% by weight, still more preferably at least 90% by weight. Examples of suitable cobalt compounds are metallic cobalt powder, cobalt hydroxide, cobalt oxide or mixtures thereof, preferred cobalt compounds are $Co(OH)_2$ or $Co_3O_4$.

The amount of cobalt compound present in the mixture may vary widely. Typically, the mixture comprises up to 60 parts by weight of cobalt per 100 parts by weight of refractory oxide, preferably 10–40 parts by weight. The above amounts of cobalt refer to the total amount of cobalt, on the basis of cobalt metal, and can be determined by known elemental analysis techniques.

The cobalt-containing catalyst or catalyst precursor prepared by the process of the present invention may comprise one or more promoter metals. Suitable promoter metals are known to those skilled in the art. Preferred promoter metals are manganese, vanadium, rhenium, ruthenium, zirconium, titanium, and chromium. A most preferred promoter metal is manganese. The promoter metal(s) or precursor(s) therefor may be added at any stage of the preparation process in the form of soluble or insoluble promoter metal compounds. Suitable promoter metal compounds are metallic powders, hydroxides, oxides, (organic acid) salts and mixtures thereof.

The amount of promoter metal in the catalyst or catalyst precursor may vary widely. Typically the catalyst or catalyst precursor comprises the promoter metal(s) in such an amount that the atomic ratio of cobalt and promoter metal(s) is at least 4, preferably at least 5, more preferably between 6 and 250.

In a preferred embodiment, at least one compound of a promoter metal is present in step (a), i.e. the mixing step, of the preparation process.

The cobalt compound which is at least partially insoluble in the liquid may be obtained by precipitation. Any precipitation method known in the art may be used. Preferably, the cobalt compound is precipitated by addition of a base or a base-releasing compound to a solution of a soluble cobalt compound, for example by the addition of sodium hydroxide, potassium hydroxide, ammonia, urea, or ammonium carbonate. Any suitable soluble cobalt compound may be used, preferably cobalt nitrate, cobalt sulphate or cobalt acetate, more preferably cobalt nitrate. Alternatively, the cobalt compound may be precipitated by the addition of an acid or an acid-releasing compound to a cobalt ammonia complex. The precipitated cobalt compound may be separated from the solution, washed, dried, and, optionally, calcined. Suitable separation, washing, drying and calcining methods are commonly known in the art.

In one embodiment of the process of the present invention, the cobalt compound and the compound of promoter metal are obtained by co-precipitation, most preferably by co-precipitation at constant pH. Co-precipitation at constant pH may be performed by the controlled addition of a base, a base-releasing compound, an acid or an acid-releasing compound to a solution comprising a soluble cobalt compound and a soluble compound of promoter metal, preferably by the controlled addition of ammonia to an acidic solution of a cobalt compound and a promoter metal compound.

The cobalt compound and, optionally, the promoter metal compound may be precipitated in the presence of at least a part of the titania or titania precursor, preferably in the presence of all titania or titania precursor. In a preferred embodiment of the invention, cobalt hydroxide and manganese hydroxide are co-precipitated by addition of ammonia to a solution comprising cobalt nitrate, manganese nitrate, and titania particles. The precipitated cobalt hydroxide and manganese hydroxide and the titania particles may be separated from the solution, washed, dried, and, optionally, calcined by methods commonly known in the art.

The solids content of the mixture formed in step (a) of the preparation process of the invention may be up to 90% by weight based on the total mixture. It will be appreciated that the mixing method largely depends on the solids contents of the mixture.

The mixing of step (a) of the catalyst preparation process of the present invention may suitably be performed by methods known to those skilled in the art, such as by kneading, mulling or stirring.

It will be appreciated that the obtained mixture may not be of the desired size and shape to serve as a catalyst carrier. Thus, a shaping step is required to prepare the catalyst or catalyst precursor. Shaping techniques are well known to those skilled in the art and include pelletising, granulating, extrusion, spray-drying, and hot oil dropping methods.

The process of the present invention involves a drying step. Typically, the compositions will be dried after shaping and before calcination. Optionally, shaping and drying can be combined in one step, for example by spray-drying. Alternatively, the mixture may be dried before shaping it, for example by drying a filter cake before crushing it. It will be appreciated that drying and calcining may be combined in one step.

In one embodiment of the invention, the solids content of the mixture obtained in step (a) of the catalyst preparation process is relatively high and therefore the mixing is suitably performed by kneading or mulling, and the thus-obtained mixture is shaped by pelletising, extrusion, granulating or crushing, preferably by extrusion. In this embodiment the solids content of the mixture is typically in the range of from 30 to 90% by weight, preferably of from 50 to 80% by weight.

Typically, the ingredients of the mixture are mulled for a period of from 5 to 120 minutes, preferably from 15 to 90 minutes. During the mulling process, energy is put into the mixture by the mulling apparatus. The mulling process may be carried out over a broad range of temperature, preferably from 15 to 90° C. As a result of the energy input into the mixture during the mulling process, there will be a rise in temperature of the mixture during mulling. The mulling process is conveniently carried out at ambient pressure. Any suitable, commercially available mulling machine may be employed.

To improve the flow properties of the mixture, it is preferred to include one or more flow improving agents and/or extrusion aids in the mixture prior to extrusion. Suitable additives for inclusion in the mixture include fatty amines, quaternary ammonium compounds, polyvinyl pyridine, sulphoxonium, sulphonium, phosphonium and iodonium compounds, alkylated aromatic compounds, acyclic mono-carboxylic acids, fatty acids, sulphonated aromatic compounds, alcohol sulphates, ether alcohol sulphates, sulphated fats and oils, phosphonic acid salts, polyoxyethylene alkylphenols, polyoxyethylene alcohols, polyoxyethylene alkylamines, polyoxyethylene alkylamides, polyacrylamides, polyols and acetylenic glycols. Preferred additives are sold under the trademarks Nalco and Superfloc.

To obtain strong extrudates, it is preferred to include in the mixture, prior to extrusion, at least one compound which acts as a peptising agent for the titania. Suitable peptising agents for inclusion in the extrudable mixture are well known in the art and include basic and acidic compounds. Examples of basic compounds are ammonia, ammonia-releasing compounds, ammonium compounds or organic amines. Such basic compounds are removed upon calcination and are not retained in the extrudates to impair the catalytic performance of the final product. Preferred basic compounds are organic amines or ammonium compounds. A most suitable organic amine is ethanol amine. Suitable acidic peptising agents include weak acids, for example formic acid, acetic acid, citric acid, oxalic acid, and propionic acid.

Optionally, burn-out materials may be included in the mixture, prior to extrusion, in order to create macropores in the resulting extrudates. Suitable burn-out materials are commonly known in the art.

The total amount of flow-improving agents/extrusion aids, peptising agents, and burn-out materials in the mixture preferably is in the range of from 0.1 to 20% by weight, more preferably from 0.5 to 10% by weight, on the basis of the total weight of the mixture.

Extrusion may be effected using any conventional, commercially available extruder. In particular, a screw-type extruding machine may be used to force the mixture through the orifices in a suitable dieplate to yield extrudates of the desired form. The strands formed upon extrusion may be cut to the desired length.

After extrusion, the extrudates are dried. Drying may be effected at an elevated temperature, preferably up to 500° C., more preferably up to 300° C. The period for drying is typically up to 5 hours, more preferably from 15 minutes to 3 hours.

In another embodiment of the invention, the solids contents of the mixture obtained in step (a) is such that a slurry or suspension is obtained, and the slurry or suspension thus-obtained is shaped and dried by spray-drying. The solids content of the slurry/suspension is typically in the range of from 1 to 30% by weight, preferably of from 5 to 20% by weight.

The thus-obtained slurry or suspension is suitably shaped and dried by spray-drying.

The extruded and dried, spray-dried or otherwise-shaped and dried compositions are subsequently calcined. Calcination is effected at elevated temperature, preferably at a temperature between 400 and 750°0 C., more preferably between 500 and 650° C. The duration of the calcination treatment is typically from 5 minutes to several hours, preferably from 15 minutes to 4 hours. Suitably, the calcination treatment is carried out in an oxygen-containing atmosphere, preferably air. It will be appreciated that, optionally, the drying step and the calcining step can be combined.

The present invention also relates to a cobalt-containing catalyst or catalyst precursor obtainable by a process as hereinbefore defined. The catalyst according to the present invention is typically used to catalyse a process for the preparation of hydrocarbons from synthesis gas. Typically, when in use in that process, at least part of the cobalt is in its metallic state.

Therefore, it is normally advantageous to activate the catalyst or catalyst precursor prior to use by a reduction treatment, in the presence of hydrogen at elevated temperature. Typically, the reduction treatment involves treating the catalyst at a temperature in the range of from 100 to 450° C. for 1 to 48 hours at elevated pressure, typically from 1 to 200 bar abs. Pure hydrogen may be used in the reduction treatment, but it is usually preferred to apply a mixture of hydrogen and an inert gas, like nitrogen. The relative amount of hydrogen present in the mixture may range between 0 and 100% by volume.

According to one preferred embodiment, the catalyst is brought to the desired temperature and pressure level in a nitrogen gas atmosphere. Subsequently, the catalyst is contacted with a gas mixture containing only a small amount of hydrogen gas, the rest being nitrogen gas. During the reduction treatment, the relative amount of hydrogen gas in the gas mixture is gradually increased up to 50% or even 100% by volume.

If possible, it is preferred to activate the catalyst in-situ, that is inside the reactor. International patent application publication No. WO 97/17137 describes an in-situ catalyst activation process which comprises contacting the catalyst in the presence of hydrocarbon liquid with a hydrogen-containing gas at a hydrogen partial pressure of at least 15 bar abs., preferably at least 20 bar abs., more preferably at least 30 bar abs. Typically, in this process the hydrogen partial pressure is at most 200 bar abs.

It is advantageous to rejuvenate spent catalyst, i.e. catalyst that has lost at least part of the initial activity of an activated fresh catalyst, by subjecting it to a ROR treatment. Typically, the ROR treatment involves the steps, in sequence, of reduction with a hydrogen-containing gas, oxidation with an oxygen-containing gas, and reduction with a hydrogen-containing gas.

In a further aspect, the invention relates to a process for the preparation of hydrocarbons, which comprises contacting a mixture of carbon monoxide and hydrogen at elevated temperature and pressure with a cobalt-containing catalyst as described hereinbefore.

The process is typically carried out at a temperature in the range from 125 to 350° C., preferably 175 to 275° C. The pressure is typically in the range from 5 to 150 bar abs., preferably from 5 to 80 bar abs., in particular from 5 to 50 bar abs.

Hydrogen and carbon monoxide (synthesis gas) is typically fed to the process at a atomic ratio in the range from 0.5 to 2.5.

The gas hourly space velocity (GHSV) of the synthesis gas in the process of the present invention may vary within wide ranges and is typically in the range from 400 to 10000 Nl/l/h, for example from 400 to 4000 Nl/l/h. The term GHSV is well known in the art, and relates to the volume of synthesis gas in Nl, i.e. liters at STP conditions (0° C. and 1 bar abs), which is contacted in one hour with one liter of catalyst particles, i.e. excluding interparticular void spaces. In the case of a fixed catalyst bed, the GHSV may also be expressed as per liter of catalyst bed, i.e. including interparticular void space.

The process for the preparation of hydrocarbons may be conducted using a variety of reactor types and reaction regimes, for example a fixed bed regime, a slurry phase regime or an ebullating bed regime. It will be appreciated that the size of the catalyst particles may vary depending on the reaction regime they are intended for. It belongs to the skill of the skilled person to select the most appropriate catalyst particle size for a given reaction regime.

Further, it will be understood that the skilled person is capable to select the most appropriate conditions for a specific reactor configuration and reaction regime. For example, the preferred gas hourly space velocity may depend upon the type of reaction regime that is being applied. Thus, if it is desired to operate the hydrocarbon synthesis process with a fixed bed regime, preferably the gas hourly space velocity is chosen in the range from 500 to 2500 Nl/l/h. If it is desired to operate the hydrocarbon synthesis process with a slurry phase regime, preferably the gas hourly space velocity is chosen in the range from 1500 to 7500 Nl/l/h.

The invention will now be illustrated further by means of the following Examples.

EXAMPLE I (Comparative)

A mixture was prepared containing 217 g alumina powder, 44 g commercially available Co(OH)2 powder, 14 g Mn(Ac)2.4H2O, 8 g HNO3 and 170 g water. The mixture was kneaded for 15 minutes. The mixture was shaped using a Bonnot extruder. The extrudates were dried for 16 hours at 120° C. and calcined for 2 hours at 500° C. The resulting extrudates contained 18 wt % Co and 2 wt % Mn.

EXAMPLE II (Comparative)

Titania extrudates were prepared as follows. Commercially available titania powder (P25 ex. Degussa) was mixed with water and ammonia. The mixture was shaped using a Bonnot extruder. The extrudates were dried for 16 hours at 120° C. and calcined for two hours at 500° C.

A solution was prepared containing 100 g Co(NO3) 2.6H2O and 4 g Mn(NO3)2.4 H2O and 10 ml of water. 70 g of the titania extrudates were impregnated with this solution in four impregnation steps. After each impregnation step the extrudates were dried at 120° C. for 16 hours and calcined at 500° C. for two hours. The resulting impregnated and calcined extrudates.

EXAMPLE III

A mixture was prepared containing 143 g commercially available titania powder (P25 ex. Degussa), 66 g commercially available Co(OH)2 powder, 10.3 g Mn(Ac)2.4H2O and 38 g water. The mixture was kneaded for 15 minutes. The mixture was shaped using a Bonnot extruder. The extrudates were dried for 16 hours at 120° C. and calcined for 2 hours at 500° C. The resulting extrudates contained 20 wt % Co and 1 wt % Mn.

EXAMPLE IV

A suspension was made containing 175 g commercially available titania powder (P25 ex. Degussa). To this suspension a solution was added containing 250 g Co(NO3)2.6H2O and 8 g Mn(NO3)2.4H2O dissolved in 500 ml water. Simultaneously, ammonia was added to the suspension to keep the pH of the suspension between 7 and 8. After the addition of the metal solution to the titania suspension, the precipitated Co and Mn on the titania was filtered and washed with water. The filter cake was dried at 120° C.

A mixture was prepared containing the dried filter cake, water and ammonia. The mixture was kneaded for 15 minutes. The mixture was shaped using a Bonnot extruder. The extrudates were dried for 16 hours at 120° C. and calcined for 2 hours at 500° C. The resulting extrudates contained 20 wt % Co and 0.8 wt % Mn.

EXAMPLE V

A suspension was made containing 175 g commercially available titania powder (P25 ex. Degussa). To this suspension a solution was added containing 250 g Co(NO3)2.6H2O and 8 g Mn(NO3)2.4H2O dissolved in 500 ml water. Simultaneously, ammonia was added to the suspension to keep the pH of the suspension between 7 and 8. After the addition of the metal solution to the titania suspension, the precipitated Co and Mn on the titania was filtered and washed with water. A suspension was made containing the filter cake and 500 g of water. The suspension was spray-dried using a Niro Atomizer. The inlet temperature was 250° C. and the outlet temperature was 120° C. The resulting particles were calcined for 1 hour at 500° C. The resulting catalyst particles contained 20 wt % Co and 1 wt % Mn.

EXAMPLE VI (Comparative)

A spray-dried titania powder was prepared as follows.

Commercially available titania powder (P25 ex. Degussa) was mixed with water. The mixture contained 30% by weight of titania powder. The mixture was spray-dried using a Niro Atomizer. The inlet temperature was 250° C. and the outlet temperature was 117° C. The resulting product was calcined for 1 hour at 500° C. The spray-dried titania particles were impregnated with a concentrated solution containing cobalt nitrate and manganese nitrate. The solution was prepared by heating solid cobalt nitrate (Co(NO3)2.6H2O) and solid manganese nitrate (Mn(NO3)2.4H2O) to a temperature of 60° C., thus causing the metal nitrates to dissolve in their own crystal water. The impregnated titania particles were dried for 2 hours at 120° C. and subsequently calcined in air for 1 hour at 400° C. The resulting catalyst particles contained 20 wt % Co and 1 wt % Mn.

EXAMPLE VII

Catalysts I, II, III and IV were tested in a process for the preparation of hydrocarbons. Micro-flow reactors containing 10 ml of catalyst extrudates I, II, II and IV, respectively, in the form of a fixed bed of catalyst particles, were heated to a temperature of 260° C., and pressurised with a continuous flow of nitrogen gas to a pressure of 2 bar abs. The catalysts were reduced in-situ for 24 hours with a mixture of nitrogen and hydrogen gas. During reduction the relative amount of hydrogen in the mixture was gradually increased from 0% to 100%. The water concentration in the off-gas was kept below 3000 ppmv.

Following reduction the pressure was increased to 26 bar abs. The reaction was carried out with a mixture of hydrogen and carbon monoxide at a H2/CO ratio of 1.1:1. The GHSV amounted to 800 Nl/l/h. The reaction temperature is expressed as the weighted average bed temperature (WABT) in ° C. The space time yield (STY), expressed as grammes hydrocarbon product per liter catalyst particles (including the voids between the particles) per hour, and the $C_5+$ selectivity, expressed as a weight percentage of the total hydrocarbon product, were determined for each experiment after 50 hours of operation. The results are set out in Table I.

TABLE I

| Catalyst | I | II | III | IV |
|---|---|---|---|---|
| WABT (° C.) | 230 | 227 | 208 | 215 |
| STY (g/l/h) | 50 | 110 | 104 | 105 |
| $C_5^+$ selectivity (%) | 72 | 80 | 94 | 90 |

It will be appreciated that the activity and selectivity of both catalyst III and IV, according to the invention, is much better than the activity and selectivity of catalysts I and II.

EXAMPLE VIII

Catalysts V and VI were tested in a process for the preparation of hydrocarbons. Micro-flow reactors containing 10 ml of catalyst particles V and VI, respectively, were heated to a temperature of 260° C., and pressurised with a continuous flow of nitrogen gas to a pressure of 2 bar abs. The catalyst were reduced in-situ for 24 hours with a mixture of nitrogen and hydrogen gas. During reduction the relative amount of hydrogen in the mixture was gradually increased from 0% to 100%. The water concentration in the off-gas was kept below 3000 ppmv.

Following reduction the pressure was increased to 26 bar abs. The reaction was carried out with a mixture of hydrogen and carbon monoxide at a H2/CO ratio of 1.7:1. The GHSV amounted to 2400 Nl/l/h. The reaction temperature is expressed as the weighted average bed temperature (WABT) in ° C. The space time yield (STY), expressed as grammes hydrocarbon product per liter catalyst particles (excluding the voids between the particles) per hour, and the C5+ selectivity, expressed as a weight percentage of the total hydrocarbon product, were determined for each experiment after 50 hours of operation. The results are set out in Table II.

TABLE II

| Catalyst | V | VI |
|---|---|---|
| WABT (° C.) | 215 | 225 |
| STY (g/l/h) | 560 | 540 |
| $C_5^+$ selectivity (%) | 89 | 88 |

It will be appreciated that catalyst V shows a better performance than catalyst VI. Further, the catalyst preparation process of Example V (according to the invention) is much simpler than the catalyst preparation process of Example VI (comparative).

We claim:

1. A process for the preparation of a cobalt-containing catalyst or catalyst precursor, the process comprising:
   (a) mixing (1) titania or a titania precursor, (2) a liquid, and (3) a cobalt compound, which is at least partially insoluble in the amount of liquid used, to form a mixture;
   (b) shaping and drying of the mixture thus-obtained; and
   (c) calcination of the catalyst or catalyst precursor thus-obtained.

2. The process of claim 1 wherein at least 50 weight percent of the cobalt compound is insoluble in the amount of liquid used.

3. The process of claim 1 wherein the cobalt compound is selected from the group consisting of metallic cobalt powder, cobalt hydroxide, and cobalt oxide.

4. The process of claim 1 wherein the cobalt compound is used in an amount of up to 60 weight percent of the amount of titania or a titania precursor.

5. The process of claim 1 wherein the catalyst or catalyst precursor comprises at least one promoter metal, the promoter selected from the group consisting of manganese, vanadium, rhenium, ruthenium, zirconium, titanium, chromium, and mixtures thereof, the promoter metal used in such an amount that the atomic ratio of cobalt to promoter metal is at least 4.

6. The process of claim 5 wherein at least one promoter metal compound is present in step (a).

7. The process of claim 1 wherein the cobalt compound is obtained by precipitation followed by calcination.

8. The process of claim 5 wherein the cobalt compound and at least one of the compounds of promoter metal are obtained by co-precipitation at constant pH.

9. The process of claim 7 wherein the cobalt compound is precipitated in the presence of at least a part of the titania or the titania precursor.

10. The process of claim 1 wherein the mixing in step (a) is performed by kneading or mulling and the mixture thus obtained is shaped by pelletising, extrusion, granulating or crushing.

11. The process of claim 10 wherein the mixture obtained has a solids content in the range of from 30 to 90% by weight.

12. The process of claim 1 wherein the mixture formed in step (a) is a slurry and the slurry thus-obtained is shaped and dried by spray-drying.

13. The process of claim 12 wherein the slurry obtained has a solids content in the range of from 1 to 30% by weight.

14. The process of claim 1 wherein the calcination is carried out at a temperature between 400 and 750° C.

15. A catalyst or catalyst precursor which is the product of a process, the process comprising:
   (a) mixing (1) titania or a titania precursor, (2) a liquid, and (3) a cobalt compound, which is at least partially insoluble in the amount of liquid used, to form a mixture;
   (b) shaping and drying of the mixture thus-obtained; and
   (c) calcination of the catalyst or catalyst precursor thus-obtained.

* * * * *